April 14, 1970 P. H. EKDAHL Plant Pat. 2,969
GERANIUM PLANT
Filed June 28, 1968
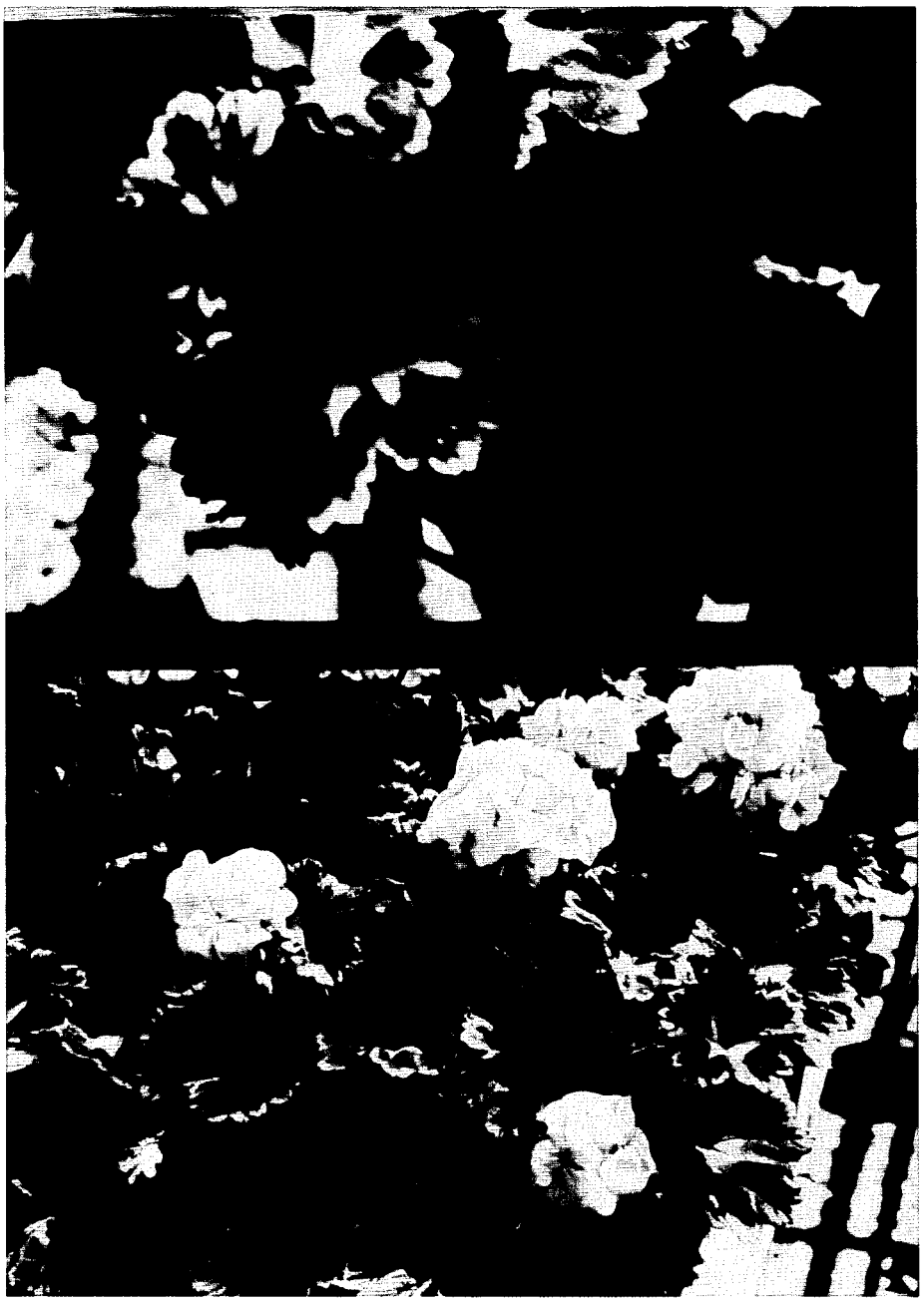
Inventor.
Paul H. Ekdahl
By: Robb & Robb
Attorneys.

United States Patent Office

Plant Pat. 2,969
Patented Apr. 14, 1970

2,969
GERANIUM PLANT

Paul H. Ekdahl, Dutch Land Road,
Freehold, N.J. 07728

Filed June 28, 1968, Ser. No. 741,145
Int. Cl. A01h *5/02*
U.S. Cl. Plt.—68 1 Claim The present invention relates to a new and distinct variety of geranium plant which was discovered by me in my greenhouses located at Freehold, N.J., as a sport of the unpatented geranium variety known as "Beaute de Poitevine."

At the time of my discovery aforesaid, I was commercially growing thousands of plants of the variety "Beaute de Poitevine," and in the course of these growing operations, my attention was attracted to one particular plant which bore some leaves which appeared to have distinctive and superior zonal markings thereon quite different from those of all the other plants in my greenhouses, as well as strikingly different from the leaves of all other geranium varieties of which I was aware. Upon close inspection of this particular plant, I found that it had sported, and I accordingly took immediate steps to preserve the sport and keep it under close observation. In due course, I took cuttings from the sport and asexually reproduced the same in my greenhouses afore-mentioned at Freehold, N.J.

Continued observation of the sport and the progeny thereof derived from the cuttings aforesaid, have convinced me that it is a new and improved geranium variety, as evidenced by the following unique combination of characteristics which are outstanding therein and which distinguish it from its parent, as well as from oll other varieties known to me:

(1) A vigorous and upright-branching plant habit;

(2) Distinctive and attractive foliage having superior zonal markings thereon which are larger than the zonal markings of the parent variety and often cover more than half the total leaf area, said markings appearing to be a very deep purple color in the early spring and when viewed from a distance of less than 20 feet, but appearing to be very black when viewed from a greater distance, and with increasing light intensity becoming deep maroon overcast with brown which persists throughout the growing season contrary to the leaves of the parent variety which almost lose their zonal coloring during the darker months of the growing season;

(3) A habit of bearing the flowers well above the foliage on strong peduncles; and (4) A distinctive, attractive and clear pink general color tonality of the flowers.

The accompanying drawing shows typical specimen plants of my new geranium variety, with some of the plants in bloom and others depicting the foliage on a slightly larger scale and in a different stage of development, all as illustrated in color.

The following is a detailed description of my new geranium variety, as based on observations of specimen plants grown in my greenhouses at Freehold, N.J., with color terminology in accordance with Nickerson's Color Fan, published by Munsell Color Company, Inc., of Baltimore, Md., except where Koster's Color Guide is indicated or where general color terms of ordinary dictionary significance are obvious:

Parentage: Sport of "Beaute de Poitevine."

Propagation: Holds its distinguishing characteristics through succeeding propagations by cuttings.

Type: Tender; for greenhouse use and also for outdoor garden decoration.

FLOWER

Flowers borne: Several to stem; in regular, rounded clusters; on strong and long stems.

Quantity of bloom: Abundant, both indoors and in greenhouse.

Continuity: Continuous.

Bud (single floret):

*Form.*—Pointed; ovoid.

*Color.*—Slightly lighter than Strong Redish-Orange Hue 7.5R 6/12.

*Sepals.*—Permanent; long (from 11 to 12 mm.); straight; spear-shaped. Color—slightly lighter than Moderate Yellow Green, Hue 5GY 5/6.

*Calyx.*—Sepals 5 in number. Color—slightly lighter than Moderate Yellow Green, Hue 5GY 5/6.

*Peduncle.*—Long; heavy; erect; stiff; rough. Color—slightly stronger than Dark Red, Hue 2.5R 3/7 when exposed to sun; slightly lighter than Moderate Yellow Green, Hue 5GY 5/6 when not exposed to sun.

*Pedicels.*—Fuzzy; erect. Length—from 27 to 28 mm. Opening—bud opens well. Petalage—semi-double, with 2 additional petals; usually 5 petals under normal conditions; no discoloration apparent.

Petals:

*Color.*—Tip of petal—slightly darker than Strong Yellowish-Pink, Hue 7.5R 7/9. Flower head—slightly lighter than Strong Reddish-Orange, Hue 7.5R 6/12.

*Texture.*—Thick.

*Form.*—Ovate, with acute base.

*Fragrance.*—Slight.

*Lasting quality.*—Long.

Genital organs:

*Stamens, anthers.*—Small; few. Color—anthers tipped with lighter than Strong Greenish-Yellow, Hue, 7.5Y 7/9, shading to slightly darker than Strong Red, Hue 5R 4/12 at base.

*Stamens, filaments.*—Short; some fused. Color—Brilliant Greenish-Yellow, Hue 7.5Y 9/8.

*Pistil, styles.*—Usually 1 in number. Color—Strong Red, Hue 5R 4/12.

*Pistil, stigmas.*—Usually 5 in number. Color—Strong Red, Hue 5R 4/12.

PLANT

Form: Upright.

Growth: Vigorous; upright-branching.

Foliage:

*Size.*—Large.

*Quantity.*—Normal.

*Color.*—New foliage: upper side—slightly lighter than Moderate Olive Green, Hue 7.5GY 4/4, with zonal markings near Dark Purple. Plate 56 (Koster), with a dark brown cast; under side—between Moderate Yellow Green, Hue 7.5GY 5/7 and Moderate Olive Green, Hue 7.5 GY 4/4; fuzzy; zonal markings not apparent on under side, but zonal markings on upper side deepen color of under side. Old foliage: upper side—slightly darker than Moderate Olive Green, Hue 7.5GY 4/4, with zonal markings appearing very black from a distance and becoming near deep maroon overlaid with dark brown with increasing light intensity; under side—Moderate Olive Green, Hue 7.5GY 4/4, with some deepening toward Grayish Olive Green, Hue 7.5GY 3/2; fuzzy; no zonal markings apparent.

*Shape.*—Generally round.

*Texture.*—Upper side—leathery; corrugated. Under side—rough.

*Margin.*—Coarsely serrate.

*Stem.*—Stiff; heavy. Size—from 65 to 75 mm. long.

General observations: The new variety most nearly resembels "Beaute de Poitevine," but its foliage has larger and darker zonal markings than those of this parent and other zonal marked varieties; leaf colors and clear flower color compliment each other and present a distinctive and very attractive appearance.

I claim:

1. A new and distinct variety of geranium plant substantially as herein shown and described, characterized particularly as to novelty by the unique combination of a vigorous and upright-branching plant habit, distinctive and attractive foliage having superior zonal markings therein which are larger than the zonal markings of the present variety and often cover more than half the total leaf area, said markings appearing to be a very deep purple color in the early spring and when viewed from a distance of less than 20 feet, but appearing to be very black when viewed from a gerater distance, and with increasing light intensity becoming deep maroon overcast with brown which persists throughout the growing season contrary to the leaves of the parent variety which almost lose their zonal coloring during the darker months of the growing season, a habit of bearing the flowers well above the foliage on strong peduncles, and a distinctive, attractive and clear pink general color tonality of the flowers.

No references cited.

ROBERT E. BAGWILL, Primary Examiner